(12) United States Patent
Shonebarger et al.

(10) Patent No.: US 11,413,070 B2
(45) Date of Patent: Aug. 16, 2022

(54) LOCKING CLAMP AND EXTERNAL FIXATION HORNS

(71) Applicant: New Standard Device, LLC, San Antonio, TX (US)

(72) Inventors: Adam P. Shonebarger, San Antonio, TX (US); Robert E. Wigginton, McKinney, TX (US); Anish D. Vaghela, Boerne, TX (US)

(73) Assignee: New Standard Device, LLC, San Antonio, TX (US)

( * ) Notice: Subject to any disclaimer, the term of this patent is extended or adjusted under 35 U.S.C. 154(b) by 0 days.

(21) Appl. No.: 17/531,907

(22) Filed: Nov. 22, 2021

(65) Prior Publication Data
US 2022/0079626 A1    Mar. 17, 2022

(51) Int. Cl.
*A61B 17/64* (2006.01)
*A61B 17/00* (2006.01)

(52) U.S. Cl.
CPC ... *A61B 17/6458* (2013.01); *A61B 2017/00477* (2013.01)

(58) Field of Classification Search
CPC .............. A61B 17/6458; A61B 17/683; A61B 17/7049; A61B 17/8665; A61B 17/8685; A61B 2017/867; A61B 2017/8675; A61B 2017/868; A61B 2017/00477
USPC ............... 606/59, 292, 306, 319, 324, 328
See application file for complete search history.

(56) References Cited

U.S. PATENT DOCUMENTS

| 4,662,365 | A | 5/1987 | Gotzen et al. |
| 6,036,691 | A * | 3/2000 | Richardson ............ A61B 17/66 606/57 |
| 8,834,467 | B2 | 9/2014 | Singh et al. |
| 10,413,328 | B1 | 9/2019 | Klein, Jr. et al. |
| 10,631,896 | B2 | 4/2020 | Venturini |
| 2003/0069580 | A1* | 4/2003 | Langmaid .......... A61B 17/6458 606/59 |

(Continued)

FOREIGN PATENT DOCUMENTS

| CN | 102860861 B1 | 1/2013 |
| CN | 106963462 A1 | 7/2017 |

(Continued)

OTHER PUBLICATIONS

Smith & Nephew; "How Do You Define Freedom"; Pub. 02144, v. 1, May 2014.

*Primary Examiner* — Eduardo C Robert
*Assistant Examiner* — David C Comstock
(74) *Attorney, Agent, or Firm* — Gregory K. Goshorn; Greg Goshorn, P.C.

(57) ABSTRACT

Provided are external fixation horns and clamp for use with struts in conjunction with external bone fixation (EBF) devices. A fixation horn is a cylindrical component intended to connect and provide further fixation locations for a half-pin clamp. A horn can be offered at various angles and lengths to best fit the application and surgeon preference. Prior to securement, the horn is positioned in the desired position and orientation relative to the half-pin clamp. Once in position, a floating collar of the horn is tightened onto the clamp. The collar compresses a serrated face of the horn with a mating serrated face of the clamp. The serrated faces of the horn and half-pin clamp are designed to lock together and resist rotational slippage during use.

12 Claims, 8 Drawing Sheets

(56) References Cited

U.S. PATENT DOCUMENTS

| | | | |
|---|---|---|---|
| 2003/0191468 A1* | 10/2003 | Hoffman | A61B 17/6466 606/59 |
| 2006/0052781 A1* | 3/2006 | Thomke | A61B 17/6466 606/59 |
| 2006/0155276 A1* | 7/2006 | Walulik | A61B 17/6441 606/59 |
| 2010/0191239 A1* | 7/2010 | Sakkers | A61B 17/6458 606/59 |
| 2014/0114310 A1 | 4/2014 | Virgen et al. | |
| 2014/0343613 A1* | 11/2014 | Eliasen | A61B 17/7034 606/278 |
| 2019/0350623 A1 | 11/2019 | Wixted | |
| 2020/0038062 A1 | 2/2020 | Erickson et al. | |
| 2020/0129207 A1* | 4/2020 | Gurevich | A61B 17/6441 |
| 2021/0378711 A1* | 12/2021 | Sanders | A61B 17/6416 |

FOREIGN PATENT DOCUMENTS

| | | |
|---|---|---|
| EP | 0490812 B1 | 6/1992 |
| EP | 1 482 845 B1 | 8/2004 |
| EP | 3 388 007 A2 | 10/2018 |
| EP | 3 372 178 A1 | 9/2019 |
| KR | 20200105352 A1 | 9/2020 |
| RU | 2375984 A1 | 3/2009 |

* cited by examiner

LOCKING CLAMP AND EXTERNAL FIXATION HORNS

FIELD OF THE DISCLOSURE

The claimed subject matter relates a clamp with attachment points for external fixation horns employed with orthopedic struts and an external bone fixation device.

BACKGROUND

External Bone Fixation (EBF) devices are employed in the treatment of bone deformity and acute trauma. Typical EBF devices use circular rings that surround a patient's limb. Adjustable connection rods and struts may be employed to connect the circular rings together. Current connection rods have only a conical range of seven degrees (7°) and struts have only forty-seven degrees (47°), which reduces the functionality of the rods and struts, limiting the ability to connect circular rings together. Half pins and wires are employed to attach the circular rings and/or struts to a patient's bone to stabilize the bone while the bone or bones are being corrected or healing. The half pins and wires attach to the EBF device and struts at one or two points and are either drilled into or through a bone.

SUMMARY

Provided are external fixation horns and clamp for use with struts in conjunction with external bone fixation (EBF) devices. A fixation horn is a cylindrical component intended to connect and provide further fixation locations for a half-pin clamp. A horn can be offered at various angles and lengths to best fit the application and surgeon preference. Prior to securement, the horn is positioned in the desired position and orientation relative to the half-pin clamp. Once in position, a floating collar of the horn is tightened onto the clamp. The collar compresses a serrated face of the horn with a mating serrated face of the clamp. The serrated faces of the horn and half-pin clamp are designed to lock together and resist rotational slippage when tightened down during use.

This summary is not intended as a comprehensive description of the claimed subject matter but, rather, is intended to provide a brief overview of some of the functionality associated therewith. Other systems, methods, functionality, features and advantages of the claimed subject matter will be or will become apparent to one with skill in the art upon examination of the following figures and detailed description.

BRIEF DESCRIPTION OF THE DRAWINGS

A better understanding of the claimed subject matter can be obtained when the following detailed description of the disclosed embodiments is considered in conjunction with the following figures.

DETAILED DESCRIPTION OF THE FIGURES

The illustrations and diagrams in the Figures illustrate the architecture, functionality, and operation of possible implementations of systems according to various embodiments of the present invention.

Figure 1:
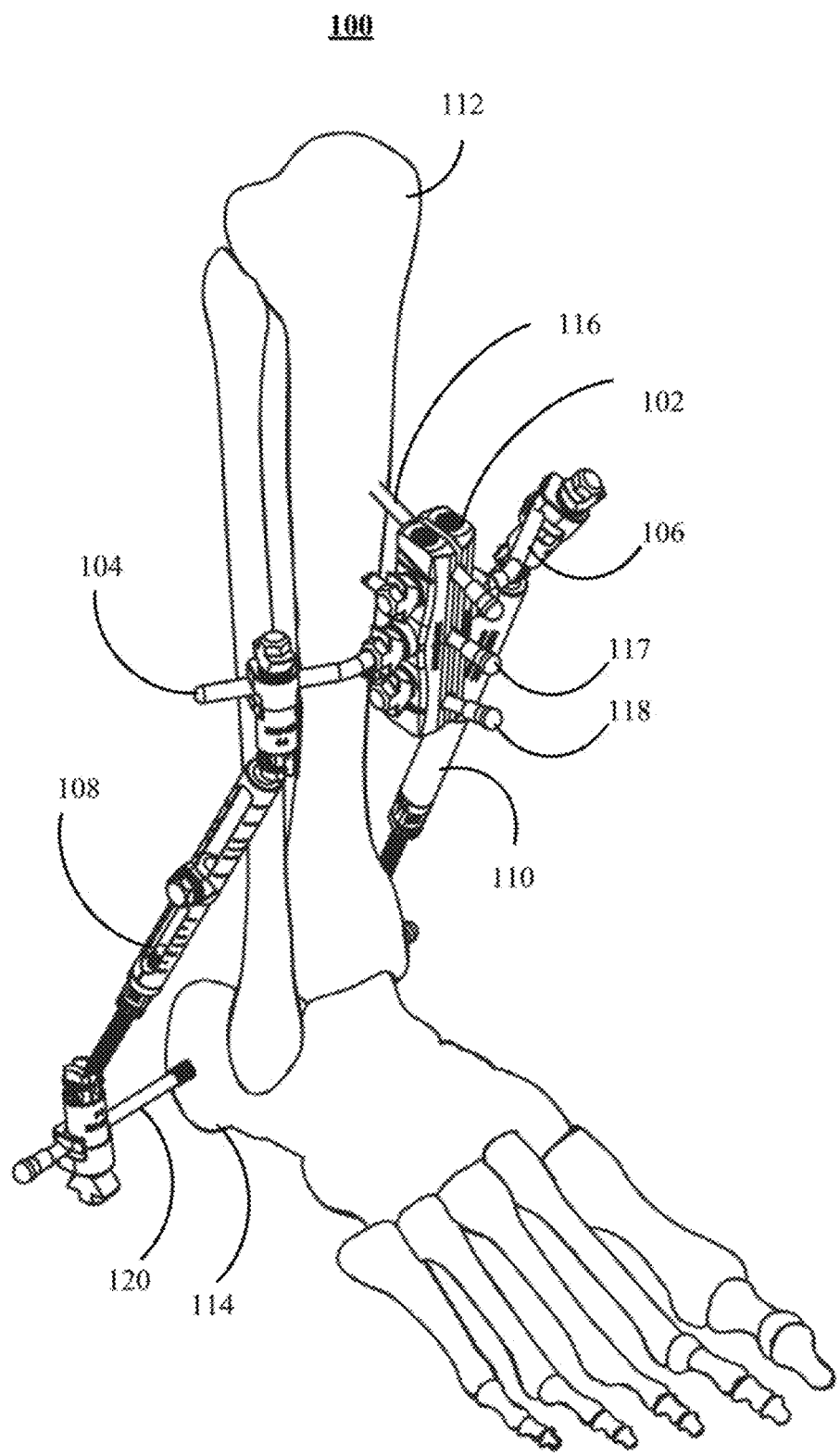
FIG. 1 is an illustration of a clamp and fixation horns employed in conjunction with an EBF device to provide support for a patient's tibia.

FIG. 1 is an illustration of a EBF device 100 employing a clamp 102 and fixation horns 104 and 106 with struts 108 and 110 providing support for a patient's lower limb consisting of a tibia 112 and heel bone, or calcaneus, 114. Tibia 112 and heel bone 114 are being secured with EBF device 100. Clamp 102 is coupled to an Angled Horn 104 and an Angled Horn 106, all in accordance with the claimed subject matter. Clamp 102 is attached to the Tibia 112 by means of half pins 116, 117, 118 securing Clamp 102 to the Tibia. Full (Shantz) Pin 120 is inserted to the Heel Bone (calcaneus) 114. One end of adjustable strut 108 is attached to Angled Horn 104 and one end of adjustable strut 110 is attached to Angled Horn 106, the opposite end of the strut 108 and 110 are attached to the ends of full pin 120. Before final bone stabilization, the assembly 100 is adjusted to correct bone alinement and then tightened in place.

Figure 2:
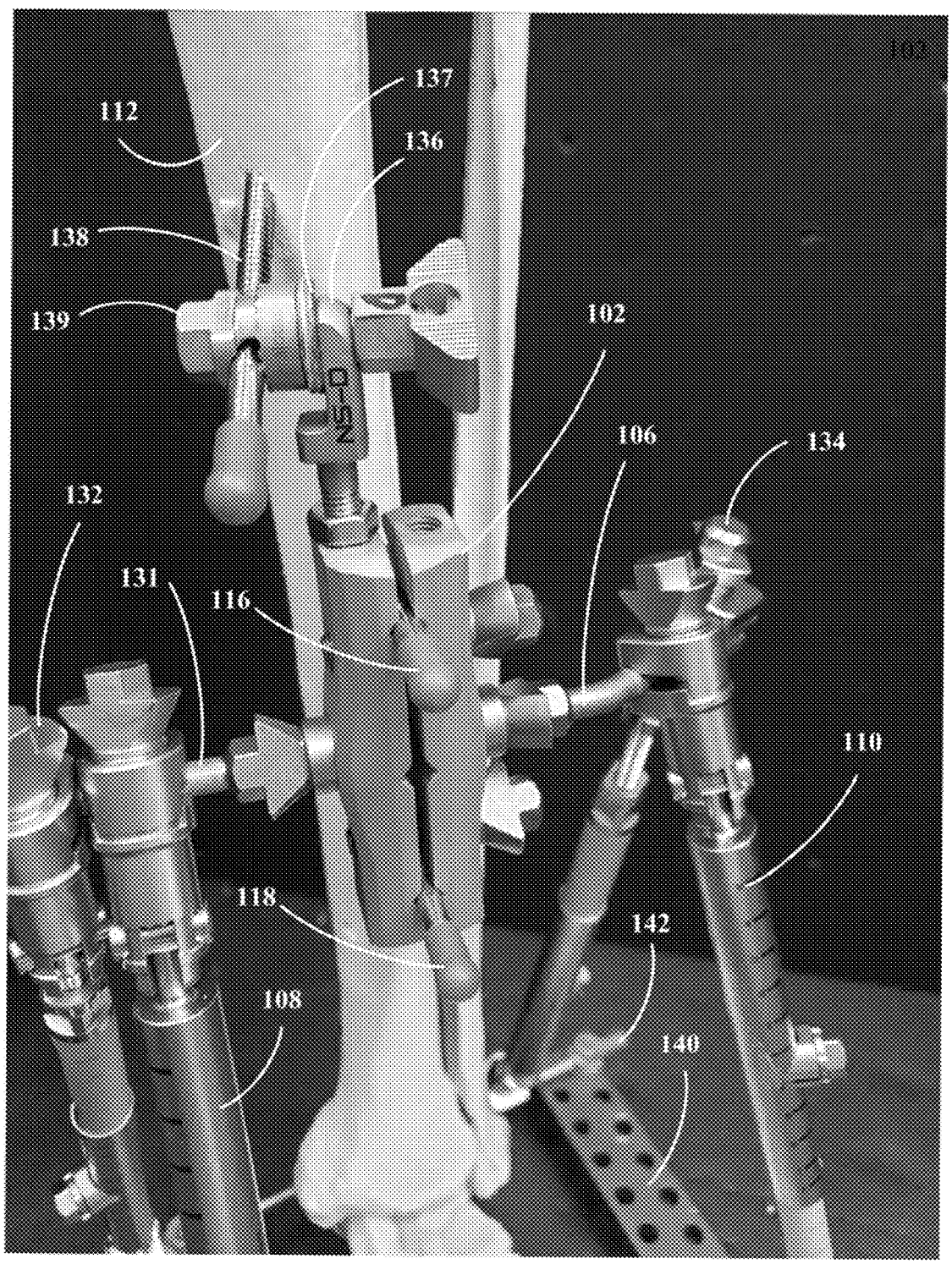
FIG. 2 is an illustration of a clamp and fixation horns similar to FIG. 1 in a different configuration.

FIG. 2 is an illustration of a clamp and fixation horns assembly 130, similar to clamp 102 and horn 106 of FIG. 1 but in a different configuration. As in FIG. 1, clamp and horns 130 are employed to correct a deformity issue with tibia 112 (FIG. 1). Clamp 102 is coupled with an Straight Horn 131 and Angled Horn 106 (FIG. 1), which are in turn coupled to adjustable struts 108 and 110 (FIG. 1), respectively. In addition, Straight Horn 131 is also attached to a second adjustable strut 132 and Angled Horn 106 is coupled to a second adjustable strut 134.

Clamp 102 is attached to tibia 112 by means of pins 116 and 118 (FIG. 1). In addition, a half pin 138 is attached to Clamp 102 by means of a half pin clamp (male hinge post) 136 and a half pin fixation bolt 139. In the illustrated configuration, struts 108, 110, 132 and 134 are attached to an orthopedic plate 140, which is coupled to a pin 142 that secures orthopedic plate 140 to heel bone 114 (FIG. 1), which is not visible in this figure.

Figure 3:
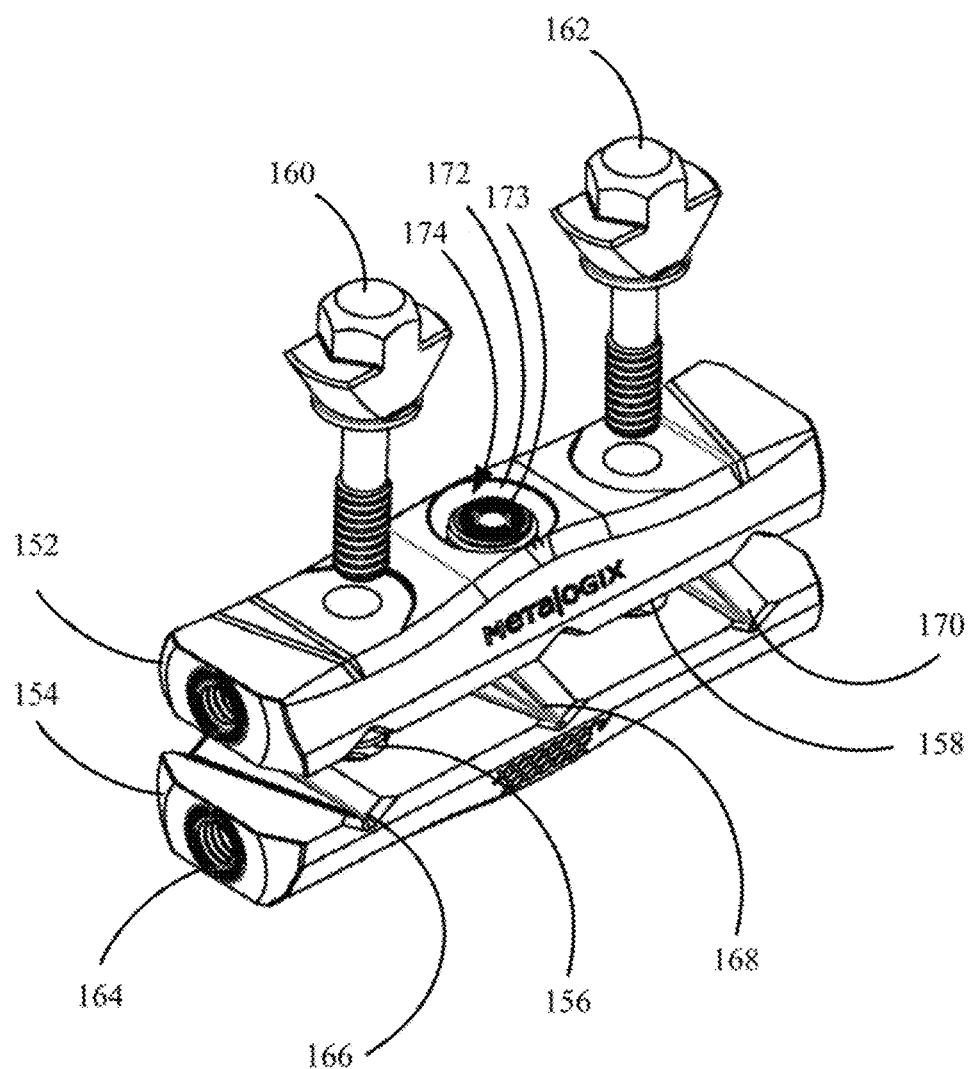
FIG. 3 is an illustration of the clamp of FIGS. 1 and 2 in greater detail.

FIG. 3 is an illustration of the clamp 102 of FIGS. 1 and 2 in greater detail. Clamp 102 includes a top clamp 152 and a bottom clamp 154. A pair of compression springs 156 and 158 push top clamp 152 and bottom clamp 154 apart to facilitate the insertion of pins such as pins 116 and 118 (FIGS. 1 and 2). A pair of clamp bolts 160 and 162 pulls top clamp 152 and bottom clamp 154 together to secure any pins.

Threaded holes 164, which for the sake of simplicity only one of which is labeled, in both ends of top clamp 152 and bottom clamp 154 enable various attachment devices, such as Male Hinge Post 136 (FIG. 2) and EBF device plates (see FIG. 9) and posts (not shown) to be attached to top and bottom clamps 152 and 154. Indentations 166, 168 and 170 in the surface of bottom clamp 154 that faces top clamp 154 as well as corresponding ones in top clamp 152, which are not labeled or visible in this figure, provide space for pins such as pins 116 and 118 to be secured by clamp 102. It should be noted that each of indentations 166, 168 and 170 include multiple channels so that pins may be positioned at various angles to clamp 102. Finally, an indented hole 174 with a threaded stud 172 with a serrated surface 173 in the surface of top clamp 152 that is away from bottom clamp 154 provides an attachment point for either Straight Horn 131 (FIGS. 2 and 3) or Angled Horn 106 (FIGS. 1 and 2). Although not visible in FIG. 3, bottom clamp 154 also includes an indented hole with a threaded stud similar to hole 172 is the surface away from top clamp 152. The attachment of horns 131 and 106 to top clamp 152 and bottom clamp 154 is described in more detail below in conjunction with FIGS. 4-6.

Figure 4:
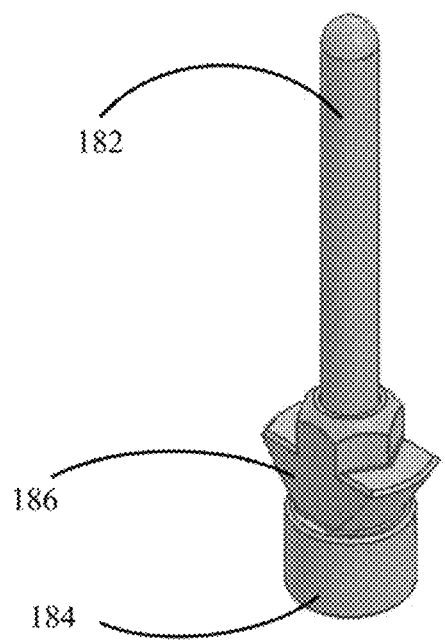
FIG. 4 is an illustration of straight fixation horn in accordance with the claimed subject matter.

FIG. 4 is an illustration of Straight Horn 131 shown above in FIGS. 2 and 3. Straight Horn 131 includes a straight horn rod 182 and a floating collar 184 with a fixation nut portion 186. Fixation nut, or tightening surfaces, 186 is tightened to secure Straight Horn 131 onto Clamp 102 (FIGS. 1-3) by tightening floating collar 184 against Clamp 102. Prior to securement, Straight Horn 131 is positioned in a desired position and orientation relative to Clamp 102 or half pin clamp 136 (FIG. 2). In one embodiment, a serrated face (see FIGS. 6 and 7) of floating collar 184 fits against a serrated surface, such as serrated surface 173 (FIG. 3). The serrated, or "poker chip," face of collar 184 and serrated, or poker chip, surface 173 lock together to resist rotational slippage when tightened down during use. Straight horn rod 182 may be offered at different lengths to best fit a particular application and surgeon preference.

Figure 5:
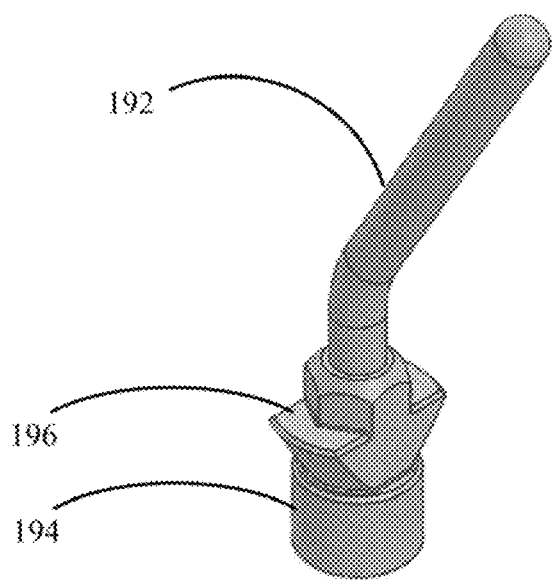
FIG. 5 is an illustration of angled fixation horn in accordance with the claimed subject matter.

FIG. 5 is an illustration of angled fixation horn 106 shown above in FIGS. 1 and 2. Angled fixation horn 106 includes an angled horn rod 192 and a floating collar 194 with a fixation nut portion 196. Fixation nut portion, or tightening surfaces, 196 is tightened to secure angled fixation horn 106 onto clamp 102 (FIGS. 1-3) or a half pin clamp such as half pin clamp 136 (FIG. 2) by compressing floating collar 184 against clamp 102 or half pin clamp 136. Prior to securement, angled fixation horn 106 is positioned in a desired position and orientation relative to clamp 102 or half pin clamp 136. In one embodiment, a serrated face (not shown) of floating collar 194 fits against a serrated surface, such as serrated surface 173 (FIG. 3). The serrated, or poker chip, face of collar 194 and serrated, or poker chip, surface 137 lock together to resist rotational slippage when tightened down during use. Angled horn rod 192 may be offered at different lengths and angles to best fit a particular application and surgeon preference.

Figure 6:
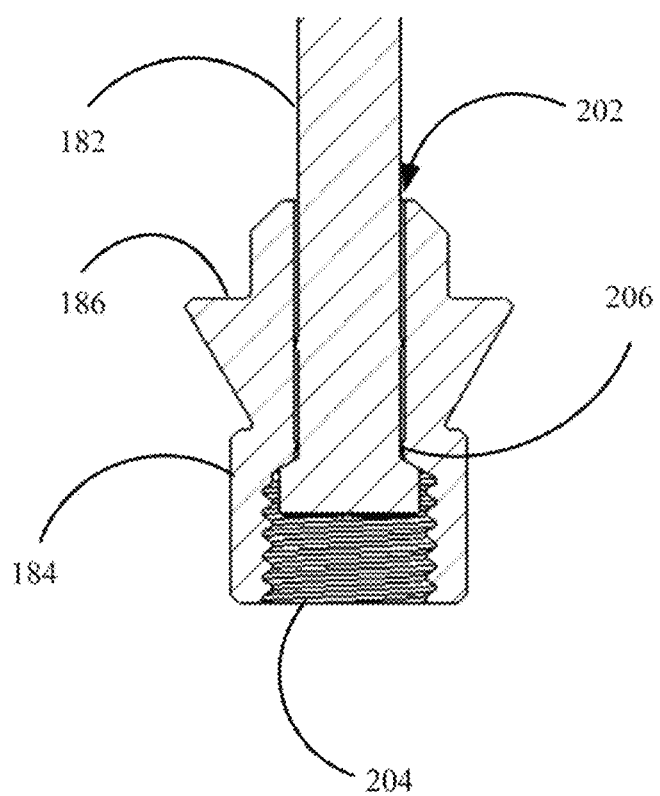
FIG. 6 is an illustration of internal portions of both the angled and straight fixation horns of FIGS. 1, 2, 4 and 5.

FIG. 6 is an cut away illustration of internal portions applicable to both straight fixation horn 131 (FIGS. 2 and 4) and angled fixation horn 106 (FIGS. 1, 2 and 5). For the sake of simplicity, this description of FIG. 6 will refer only to straight fixation horn 131. Shown are cut away portions of straight horn rod 182 (FIG. 4) and collar 184 with fixation nut portion 186 (FIG. 4). Horn rod 182 fits through a hole 202 in collar 184. A lower portion 204 of hole 202 is threaded to enable straight fixation horn 131 to be screwed on to a threaded stud, such as threaded stud 173 (FIG. 3). Above lower portion 204 of hole 202 is a press fit portion 206 that enables horn rod 182 to be more secure and still rotate while collar 184 is tightened to force floating collar 184 against a clamp such as clamp 102 (FIGS. 1-3).

Figure 7:
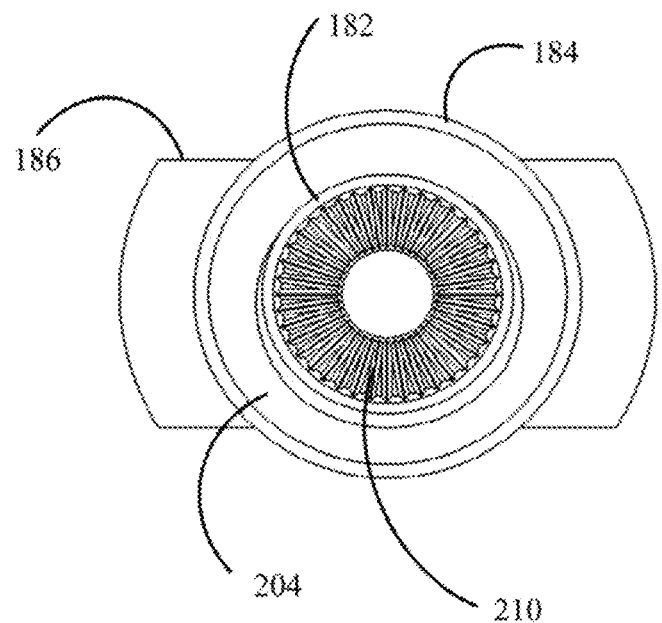
FIG. 7 illustrates a bottom, serrated surface of the fixation horns of FIGS. 1, 2, 4, 5 and 6.

FIG. 7 illustrates a bottom, serrated surface 210 of the fixation horns 106 and 131 of FIGS. 1, 2, 4, 5 and 6. In this example, horn rod 182 (FIGS. 4 and 6) is extended through the lower portion 204 (FIG. 6) in floating collar 184 (FIGS. 4 and 6) and fixation nut portion 186 (FIGS. 4 and 6) of floating collar 184. As explained above in conjunction with FIG. 6, serrated, or poker chip, surface 210 of fixation rod 182 locks together with surface 173 (FIG. 3) to resist rotational slippage when tightened down during use.

Figure 8:
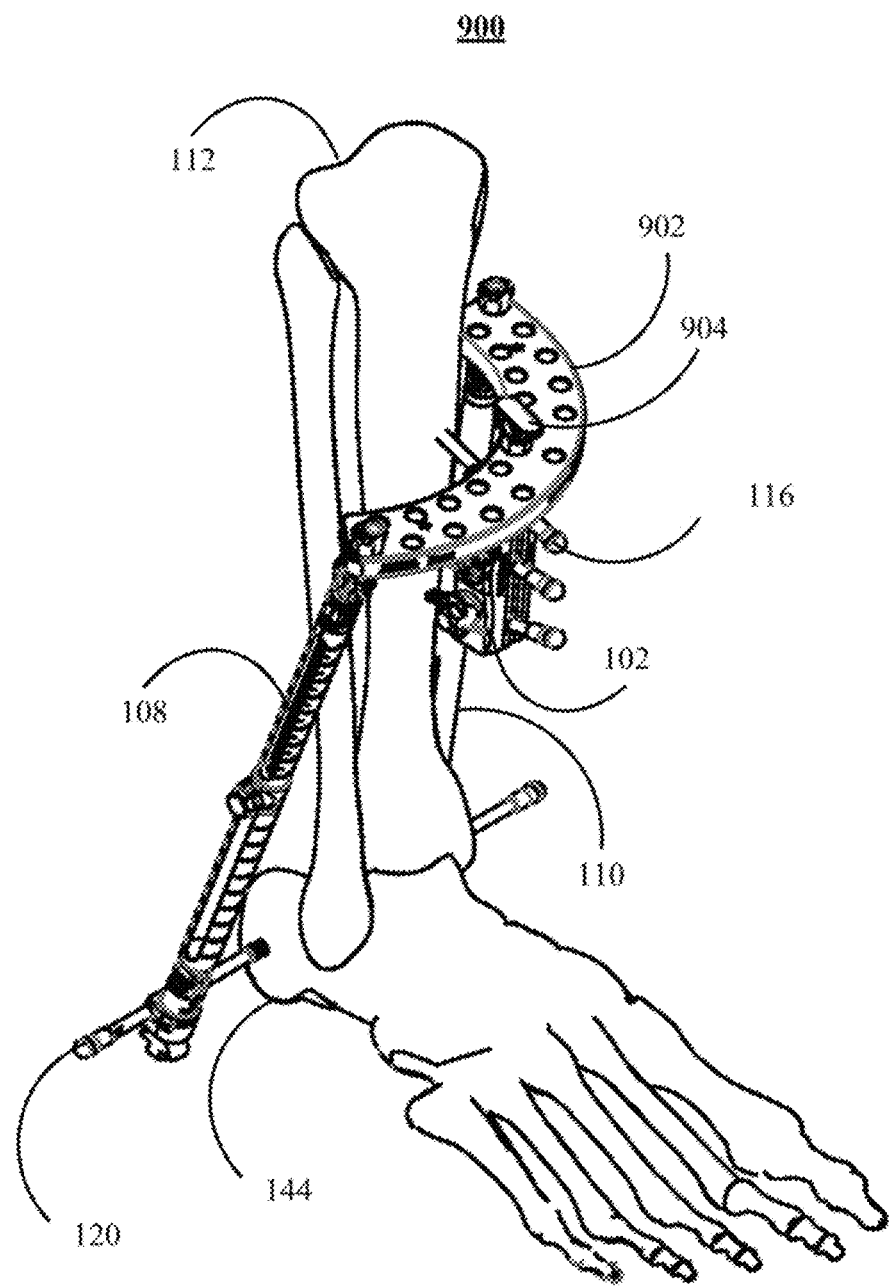
FIG. 8 is an illustration of a clamp and fixation horns employed in conjunction a second EBF device to provide support for a patient's tibia.

FIG. 8 is an illustration of a second EBF device 900 employing a clamp 102 and struts 108 and 110 providing support for a patient's lower limb consisting of a tibia 112 and heel bone, or calcaneus, 114, all of which were introduced above in conjunction with FIG. 1. Tibia 112 and heel bone 114 are being secured with EBF device 900. Clamp 102 is coupled to an EBF plate 902 by means of a bolt 904 screwed into a threaded hole such as threaded hole 164 (FIG. 3). Clamp 102 is attached to the Tibia 112 by means of half pins 116 (FIG. 1), only one of which if labeled securing Clamp 102 to Tibia 112. Full (Shantz) Pin 120 (FIG. 1) is inserted to the Heel Bone (calcaneus) 114. Before final bone stabilization, the assembly 900 is adjusted to correct bone alinement and then tightened in place.

While the claimed subject matter has been shown and described with reference to particular embodiments thereof, it will be understood by those skilled in the art that the foregoing and other changes in form and detail may be made therein without departing from the spirit and scope of the claimed subject matter, including but not limited to additional, less or modified elements and/or additional, less or modified blocks performed in the same or a different order.

We claim:

1. A fastening clamp for the external fixation of bones, comprising:
    a top clamp;
    a bottom clamp;
    a plurality of clamping bolts adapted to secure the top clamp and bottom clamp with respect to each other;
    a hole on a surface of the top clamp opposite the bottom clamp, the hole comprising a threaded rod within the hole;
    a floating collar comprising:
        a threaded shaft adapted to screw onto the threaded rod; and
        a plurality of tightening surfaces; and
    a plurality of fixation horns, each fixation horn comprising a horn rod adapted to pass through the threaded shaft, protect from the collar opposite the threaded rod, and be secured with respect to the top clamp when the floating collar is tightened against a bottom of the hole.

2. The fastening clamp of claim 1, further comprising;
    a first serrated surface on an end of the horn rod that fits into the threaded shaft; and
    a second serrated surface on the bottom of the threaded hole, adapted to correspond to the first serrated surface such that the horn rod is unable to rotate when the floating collar is tightened against the top clamp.

3. The fastening clamp of claim 1, wherein one of the plurality of horn rods is straight.

4. The fastening clamp of claim 1, wherein one of the plurality of horn rods is angled.

5. The fastening clamp of claim 1, each clamp comprising:
    an inner surface and an outer surface, wherein the inner surfaces are configured to face each other; and
    a plurality of indentations on the inner surfaces,
        wherein the indentations traverse the width of the clamping elements,
        wherein each indentation is positioned across from a corresponding indentation on an opposing clamping element, and wherein opposing indentations are adapted to secure fixation elements of an external fixation bone fixation device when the clamping elements are compressed together.

6. The fastening clamp of claim 1, further comprising a plurality of springs positioned between the two clamping elements and adapted to push the two clamping elements apart.

7. An External Bone Fixation (EBF) device, comprising:
a plurality of plates;
a plurality of adjustable struts; and
a fastening clamp, comprising:
  a top clamp;
  a bottom clamp;
  a plurality of clamping bolts adapted to secure the top clamp and bottom clamp with respect to each other;
  a hole on a surface of the top clamp opposite the bottom clamp, the hole comprising a threaded rod within the hole;
  a floating collar comprising:
    a threaded shaft adapted to screw onto the threaded rod; and
    a plurality of tightening surfaces; and
  a plurality of fixation horns, each fixation horn comprising a horn rod adapted to pass through the threaded shaft, project from the collar opposite the threaded rod, and be secured with respect to the top clamp when the floating collar is tightened against a bottom of the hole.

8. The fastening clamp of claim 7, further comprising:
a first serrated surface on an end of the horn rod that fits into the threaded shaft; and
a second serrated surface on the bottom of the threaded hole, adapted to correspond to the first serrated surface such that the horn rod is unable to rotate when the floating collar is tightened against the top clamp.

9. The fastening clamp of claim 7, wherein one of the plurality of horn rods is straight.

10. The fastening clamp of claim 7, wherein one of the plurality of horn rods is angled.

11. The fastening clamp of claim 7, each clamp comprising:
an inner surface and an outer surface, wherein the inner surfaces are configured to face each other; and
a plurality of indentations on the inner surfaces,
wherein the indentations traverse the width of the clamping elements,
wherein each indentation is positioned across from a corresponding indentation on an opposing clamping element, and
wherein opposing indentations are adapted to secure fixation elements of an external fixation bone fixation device when the clamping elements are compressed together.

12. The fastening clamp of claim 7, further comprising a plurality of springs positioned between the two clamping elements and adapted to push the two clamping elements apart.

* * * * *